United States Patent
Carlsen et al.

(10) Patent No.: US 9,842,190 B2
(45) Date of Patent: Dec. 12, 2017

(54) DISPLAYING A SET OF INTERRELATED OBJECTS

(75) Inventors: Ingwer-Curt Carlsen, Hamburg (DE); Sebastian Peter Michael Dries, Hamburg (DE); Roland Johannes Opfer, Hamburg (DE); Arvid Randal Nicolaas, Tilburg (NL); Robbert Christiaan Van Ommering, Hapert (NL)

(73) Assignee: Koninklijke Philips N.V., Eindhoven (NL)

( * ) Notice: Subject to any disclaimer, the term of this patent is extended or adjusted under 35 U.S.C. 154(b) by 661 days.

(21) Appl. No.: 14/004,424

(22) PCT Filed: Feb. 29, 2012

(86) PCT No.: PCT/IB2012/050937
§ 371 (c)(1),
(2), (4) Date: Sep. 11, 2013

(87) PCT Pub. No.: WO2012/123842
PCT Pub. Date: Sep. 20, 2012

(65) Prior Publication Data
US 2014/0006989 A1 Jan. 2, 2014

(30) Foreign Application Priority Data
Mar. 11, 2011 (EP) ..................................... 11157885

(51) Int. Cl.
*G06F 3/048* (2013.01)
*G06F 19/00* (2011.01)
*G06F 3/0481* (2013.01)

(52) U.S. Cl.
CPC ............ *G06F 19/34* (2013.01); *G06F 3/0481* (2013.01); *G06F 19/325* (2013.01)

(58) Field of Classification Search
CPC .............................. G06F 3/0481; G06F 3/0485
(Continued)

(56) References Cited

U.S. PATENT DOCUMENTS 7,707,503 B2 * 4/2010 Good et al. ................... 715/732
2004/0088678 A1 5/2004 Litoiu et al.
(Continued)

FOREIGN PATENT DOCUMENTS

CN 101187864 A 5/2008
JP H11119969 A 4/1999
(Continued)

OTHER PUBLICATIONS

Cabitza, F. et al. "ProDoc: an Electronic Patient Record to Foster Process-Oriented Practices". Universita degli Studi di Milano-Bicocca, Milano, Italy, (2008).

*Primary Examiner* — Matthew Ell (57) ABSTRACT

A system for displaying a set of interrelated objects comprises an initializer (1) for identifying a plurality of interrelated objects, a first information filter (2) for selecting a first subset of the plurality of interrelated objects for display based on a first information filter setting, a first displayer (3) for displaying the first subset of the plurality of interrelated objects on a first display area, a user interface (7) for enabling a user to select a region of the first display area for enlargement by visually indicating the region in the first display area, wherein the user can select the region independently of locations of the displayed objects in the first display area, a second information filter (4) for selecting a second subset of the plurality of interrelated objects for display based on a second information filter setting, wherein the second information filter is arranged for selecting objects corresponding to the selected region with an increased level of information detail compared to the first information filter, (Continued)

and a second displayer (5) for displaying the second subset of the plurality of interrelated objects on a second display area.

17 Claims, 4 Drawing Sheets

(58) Field of Classification Search
USPC .......................................................... 715/769
See application file for complete search history.

(56) References Cited

U.S. PATENT DOCUMENTS

| 2005/0273738 | A1* | 12/2005 | Byrn et al. ........................ 716/4 |
| 2006/0020904 | A1 | 1/2006 | Aaltonen et al. |
| 2007/0245300 | A1 | 10/2007 | Chan et al. |
| 2008/0086684 | A1 | 4/2008 | Hertel et al. |
| 2008/0097733 | A1* | 4/2008 | Alsafadi ............... G06F 19/325 703/6 |
| 2008/0097965 | A1 | 4/2008 | Alsafadi |
| 2010/0077304 | A1* | 3/2010 | Zaman et al. ................ 715/702 |

FOREIGN PATENT DOCUMENTS

| JP | 2001249747 A | 9/2001 |
| WO | 2004053624 A2 | 6/2004 |

* cited by examiner

DISPLAYING A SET OF INTERRELATED OBJECTS

This application is a national stage application under 35 U.S.C. §371 of International Application No. PCT/IB2012/050937 filed on Feb. 29, 2012 and published in the English language on Sep. 20, 2012 as International Publication No. WO/2012/123842, which claims priority to European Application No. 11157885.2 filed on Mar. 11, 2011, the entire disclosures of which are incorporated herein by reference.

FIELD OF THE INVENTION

The invention relates to displaying a set of interrelated objects.

BACKGROUND OF THE INVENTION

Computerized clinical guidelines and pathways are becoming important tools for care providers when providing patient care and ensuring quality of care. Guidelines define the usually disease-specific clinical state-of-the-art for patient management, whereas pathways track individual patients through the multitude of available management options offered by the guidelines. Both guidelines and pathways are becoming part of hospital-wide information management systems and electronic medical records to ensure that disease and patient management follow evidence-based practice and adhere to quality standards. With growing complexity and penetration of clinical practice, the amount of information handled by these systems is growing rapidly. Intelligent means supporting user-oriented display and navigation of these data sets become more important, especially in view of the workload and time constraints under which clinical personnel make use of such systems.

Conventional flow-chart-like visual representations of computerized guidelines and pathways often become complex and unwieldy to navigate. The user either lacks information because of high-level and simplified overview representations of a guideline or pathway, or is overwhelmed by the complexity of information.

SUMMARY OF THE INVENTION

It would be advantageous to have an improved way of displaying and/or navigating a set of interrelated objects. To better address this concern, a first aspect of the invention provides a system comprising:

an initializer for identifying a plurality of interrelated objects;

a first information filter for selecting a first subset of the plurality of interrelated objects for display based on a first information filter setting;

a first displayer for displaying the first subset of the plurality of interrelated objects on a first display area;

a user interface for enabling a user to select a region of the first display area for enlargement by visually indicating the region in the first display area, wherein the user can select the region independently of locations of the displayed objects in the first display area;

a second information filter for selecting a second subset of the plurality of interrelated objects for display based on a second information filter setting, wherein the second information filter is arranged for selecting objects corresponding to the selected region with an increased level of information detail compared to the first information filter; and a second displayer for displaying the second subset of the plurality of interrelated objects on a second display area.

The system makes it easy to navigate complex data structures including a plurality of interrelated objects. The first displayer provides a high-level overview by hiding the more detailed information. However, the user interface, the second information filter, and the second displayer provide a magnifying glass functionality by enabling the user to select a region for enlargement. The user can indicate in a highly intuitive and flexible way which portion of the interrelated objects he or she would like to see with an increased level of information detail, by merely indicating a region in a visualization of the plurality of interrelated objects. It is not necessary to request an individual object to be expanded. Instead, a region of the display can be indicated. This provides more flexibility to visualize, for example, also interrelations between objects with an increased level of information detail.

The user interface may be arranged for enabling the user to select a further region of the first display area for enlargement while the second subset of the plurality of interrelated objects is being displayed on the second display area. The ability to repeatedly enable the indication of a region makes it easy for the user to quickly view all the detail he or she needs to perform his or her task. This further improves the user friendliness and efficiency of the navigation of the objects. When the inspection of the second subset of the plurality of interrelated objects gives rise to an enquiry about another region of the first display area, this can be requested without delay or further user interaction. The further region is then subjected to the second information filter and the result is displayed on the same second display area or another second display area. For example, the second display area may be a fixed display area of a display device. In another example, the second display area may move along with the currently selected region of the first display area.

The first and/or the second information filter may be arranged for filtering the objects, also based on a task or role of the user or on a particular state of a machine.

The second display area may be centered around the region of the first display area. This improves efficient navigation, because the user does not need to move the focus of his or her eyes to another region of the screen if the second display area is centered around the selected region.

The user interface may be arranged for enabling the user to drag the region over the first display area. This allows quick and intuitive navigation of the data objects. The second display area may be arranged for updating the display of the second display area in response to a drag operation of the user. This further increases the efficiency and quickness of the navigation.

It is possible that at least one of the plurality of interrelated objects is a composite object comprising a plurality of sub-objects. The first information filter may be arranged for selecting the composite object, and the second information filter may be arranged for selecting the composite object as well as at least one of the plurality of sub-objects comprised in the composite object. This is an example of two information filter settings in which the second information filter setting provides more detailed information than the first information filter setting. The different levels of information detail provided are easy to comprehend.

The plurality of interrelated objects may be associated with respective object information detail levels. The initializer may be arranged for identifying a first information detail level threshold and a second information detail level threshold. The first information filter may be arranged for selecting the objects by comparing the respective object information detail levels with the first information detail level threshold. The second information filter may be arranged for selecting the objects by comparing the respective object information detail levels with the second information detail level threshold. This is a universally applicable framework for filtering the objects.

The information represented by an interrelation between two objects may be associated with a higher information detail level than the information represented by at least one of the two objects. This is another example of different levels of information detail, wherein the more detailed interrelations are made visible only in the second display area. It is possible that some of the relations are shown in the first display area also, but some of the more detailed or less important relations are only shown in the second display area.

A piece of textual information represented by at least one of the objects may be selected by the second information filter but not by the first information filter. Other properties of the object, such as object type and/or interrelations of the object, may be selected by the first information filter also. This allows saving display space in the first display area, and allows access to the textual information by means of the second display area.

The set of interrelated objects may represent a clinical guideline. A simplified high-level overview of the parts of the clinical guideline that are outside the current focus of user attention may be combined with detailed information relevant to the current focus of user attention. The system can be used by clinical personnel for care management as well as by patients, when it is integrated into their browser, which allows patients to actively participate in their personal care management. However, other applications of the system may also be realized, as will be elucidated hereinafter.

The second information filter may be arranged for selecting objects not comprised in the first subset of objects, but interrelated with at least one object of the first subset of objects. For example, some of the objects are hidden in the first display area; these objects may be made visible in the second display area.

The first display area displayer and the second display area displayer may be arranged for displaying the objects by means of symbols and displaying the interrelations between the objects by means of lines or arrows between the objects. This may be a convenient way to display for example a flow chart or a clinical guideline.

The first displayer may be arranged for maintaining display of the objects displayed on at least part of the first display area while the second displayer is displaying the second subset of the plurality of interrelated objects on the second display area. This makes it easier to select a further region. For example, if the second display area overlaps a part of the first display area, display of the objects displayed on a non-overlapped portion of the first display area is maintained.

In another aspect, the invention provides a workstation comprising a monitor for displaying the first and second display area, as well as the system set forth.

In another aspect, the invention provides a method of displaying a set of interrelated objects, comprising:
identifying a plurality of interrelated objects;
selecting a first subset of the plurality of interrelated objects for display based on a first information filter setting;
displaying the first subset of the plurality of interrelated objects on a first display area;
enabling a user to select a region of the first display area for enlargement by visually indicating the region in the first display area, wherein the user can select the region independently of locations of the displayed objects in the first display area;
selecting a second subset of the plurality of interrelated objects for display based on a second information filter setting, wherein the second information filter setting causes selection of objects corresponding to the selected region with an increased level of information detail compared to the first information filter setting; and
displaying the second subset of the plurality of interrelated objects on a second display area;
enabling the user to select a further region of the first display area for enlargement while the second subset of the plurality of interrelated objects is being displayed on the second display area.

In another aspect, the invention provides a computer program product comprising instructions for causing a processor system to perform the method set forth.

It will be appreciated by those skilled in the art that two or more of the above-mentioned embodiments, implementations, and/or aspects of the invention may be combined in any way deemed useful.

Modifications and variations of the workstation, the system, the method, and/or the computer program product, which correspond to the described modifications and variations of the system, can be carried out by a person skilled in the art on the basis of the present description.

BRIEF DESCRIPTION OF THE DRAWINGS

These and other aspects of the invention are apparent from and will be elucidated with reference to the embodiments described hereinafter.

DETAILED DESCRIPTION OF EMBODIMENTS

Figure 1:
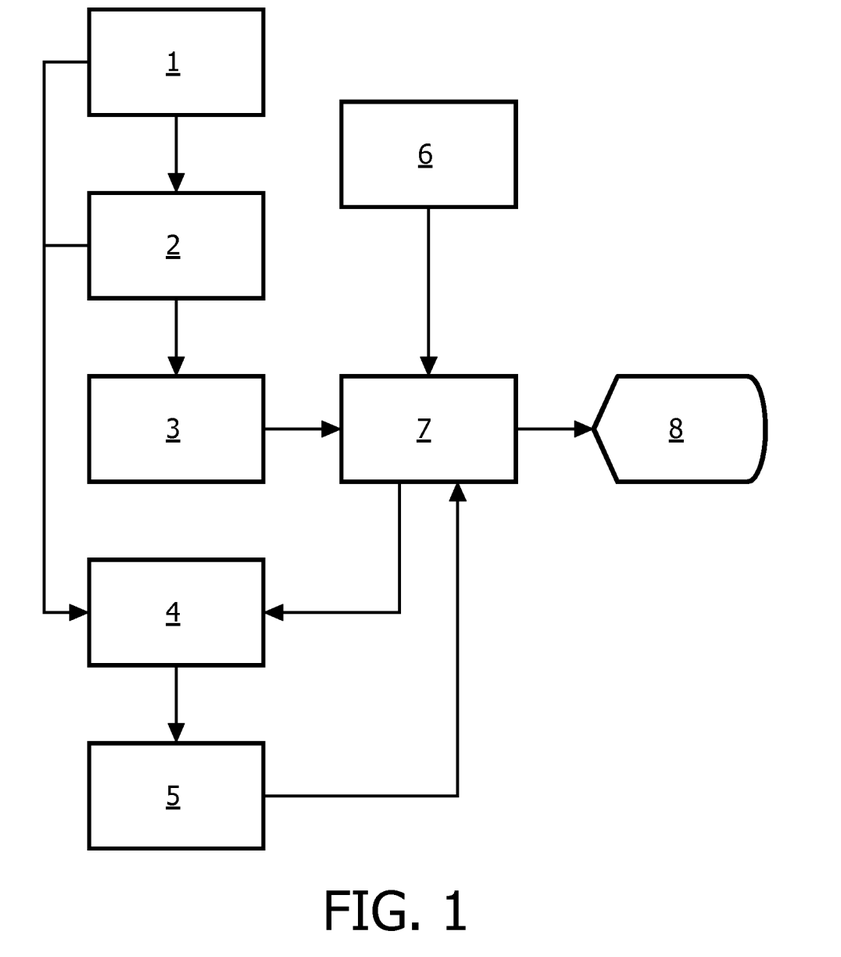
FIG. 1 is a block diagram of a system for displaying a set of interrelated objects.

FIG. 1 illustrates a system for displaying a set of interrelated objects. Such a system may be implemented, for example, in form of a suitably programmed computer system. Such a computer system may comprise a distributed system or a standalone computer or workstation. The computer system may comprise a user input device 6, such as a mouse and/or a keyboard. The computer system may further comprise a display 8. Alternatively, connectors for such peripherals may be provided. The system may further comprise storage means and/or data communication facilities to enable retrieving the data objects to be visualized.

The system may comprise an initializer 1 arranged for identifying a plurality of interrelated objects. These objects may be retrieved from a database, for example. The objects may represent elements of a clinical guideline, for example, or elements of an electronic patient record or personal health record.

The system may comprise a first information filter 2 arranged for selecting a first subset of the plurality of interrelated objects. The selection may be performed based on a first information filter setting. The first information filter setting may, for example, comprise a list of data object types to be included and/or a list of data object types to be excluded. Other kinds of filter settings may be provided by the skilled person in view of the present description.

The system may comprise a first displayer 3 arranged for displaying the first subset of the plurality of interrelated objects on a first display area. The first displayer 3 may be operatively connected to a user interface 7, for example a graphical user interface (GUI). The user interface 7 in turn may control a graphical hardware interface that may be connected to a display device 8, for example an LCD monitor. The first displayer 3 may control the user interface 7 to display the first subset of the plurality of interrelated objects on a first display area of the display device 8.

The user interface 7 may be configured to enable a user to select a region of the first display area for enlargement. This can be done using a user input device 6. User input device 6 may comprise any user input device known in the art, including for example a keyboard, mouse, and/or touch screen. The user interface 7 may be configured to provide visual feedback during the selection of the region, by means of the display device 8. For example, a region may be indicated on the display device 8 by drawing a bounding box. The indication of the region may be updated in response to user inputs such as mouse move events. The selection may be confirmed by another user input such as a mouse click. This way, the user is enabled to visually indicate the region in the first display area. The user can select the region independently of locations of the displayed objects in the first display area. For example, the region may be drawn freely as a sub-area of the first display area. Alternatively, the region may be dragged freely around the first display area. Any zero, one or more of the displayed objects can fall within the region selected by the user.

The system may comprise a second information filter 4 arranged for selecting a second subset of the plurality of interrelated objects for display. The second information filter 4 performs its filtering task based on a second information filter setting. The second information filter 4 could be implemented using the same software code as the first information filter, yet applying the second information filter setting instead of the first information filter setting. The second information filter may be arranged for selecting objects corresponding to the selected region with an increased level of information detail compared to the first information filter. Consequently, objects that are not shown in the first display area, but that logically would have been drawn inside the selected region of the first display area if the second information filter setting had been applied by the first information filter, may be selected by the second information filter.

The system may comprise a second displayer 5 arranged for displaying the second subset of the plurality of interrelated objects on a second display area. For example, the second display area shows the same objects as the objects visible in the selected region of the first display area, but enlarged. In addition, the second display area shows more detail of the objects, for example additional objects relating to the objects visible in the first display area that were not shown on the first display area may be shown in the second display area, utilizing the enlarged scale.

The user interface 7 may be arranged for enabling the user to select a further region of the first display area for enlargement while the second subset of the plurality of interrelated objects is being displayed on the second display area. The user interface 7 may be arranged for enabling the user to select any number of such further regions. The user interface 7 forwards the information describing these further regions to the second information filter 4 as soon as the user has selected the further region. The second information filter 4 processes its filtering operation for the selected further region and the second displayer causes display of the filtered objects. The second displayer may be arranged for replacing the previous second display area with the new second display area. For example, the second display area may move along with the selected region. More particularly, the second display area may be centered around the region of the first display area. Alternatively, the information may be updated in a second display area that remains positioned in a fixed portion of the screen.

The user interface 7 may be arranged for enabling the user to drag the region over the first display area to select the further regions. This may be realized by a mouse device or by a touch screen device, for example. The first information filter 4 and the second displayer 5 may be arranged for updating the display of the second display area in response to the drag operation of the user. This way, it is possible to give the system the appearance of a natural "magnifying glass", which can be hovered around a surface and gives updated magnified views in (almost) real-time.

One or more of the plurality of interrelated objects may be composite objects. Such a composite object comprises a number of sub-objects. For example, an object may comprise a container for several sub-objects. For example, an object may comprise a database record comprising several fields. Each field may be configured to comprise a particular type of information, such as a medical finding or a prescription or a medical image. It is possible to configure the first information filter in such a way that the presence and/or the kind of object and some or all of its interrelations with other objects is selected for the first subset. Also, some of the sub-objects may be selected in the first subset, whereas some other sub-objects may be omitted from the first subset. The second information filter may be arranged for including some or more of the omitted sub-objects in the second subset. This inclusion or exclusion of objects and/or sub-objects in the first and second subsets is performed under control of the first and second information filter settings. These settings may be adapted according to the information needs of the person viewing the information.

It is possible that the information stored in the objects is associated with detail information, e.g. an object information detail level. Such an object information detail level may be a numeric value assigned to an object, based on predetermined importance criteria. Alternatively, the detail information may be based on an object hierarchy imposed by a structure of objects, sub-objects, sub-sub-objects, and so on. Herein, the top level (objects) may be associated with a lower object information detail level than sub-objects, and sub-objects may be associated with a lower object information detail level than sub-sub-objects. Also, the information represented by an interrelation between two objects may be associated with a higher information detail level than the information represented by at least one of the two objects. The information filters may express inclusion criteria in terms of the information detail levels. The first information filter 2 may be arranged for selecting the objects by comparing the respective object information detail levels with the first information detail level threshold. The second information filter 4 may be arranged for selecting the objects by comparing the respective object information detail levels with the second information detail level threshold. The initializer may set these levels, based on predetermined values. Alternatively, the first information detail level threshold may be set based on the size of the first display area. Also, the number of objects may be taken into account. For the second information detail level threshold, the size of the second display area and the size of the selected region may be taken into account.

It is also possible that the second information filter 4 selects text objects stored within objects, wherein the objects are members of the first subset, but the text objects are not.

It is also possible to arrange the second information filter 5 for selecting objects not comprised in the first subset of objects, but interrelated with at least one object of the first subset of objects. This way, less important objects can be omitted in the first display area, while providing the user easy access to those objects by appropriately selecting a region.

The set of interrelated objects may represent a clinical guideline. The first displayer 3 and/or the second displayer 5 may be arranged to display the set of interrelated objects at least partly in form of a flowchart.

The first displayer 3 may be arranged for maintaining display of the objects displayed on at least part of the first display area while the second displayer 5 is displaying the second subset of the plurality of interrelated objects on the second display area. The second display area may be an overlay on top of the first display area.

The system could also be applied to geographic data, such as maps. The set of interrelated objects could comprise representations of geographic entities, wherein the interrelations define relative positions of the geographic entities.

Figure 2:
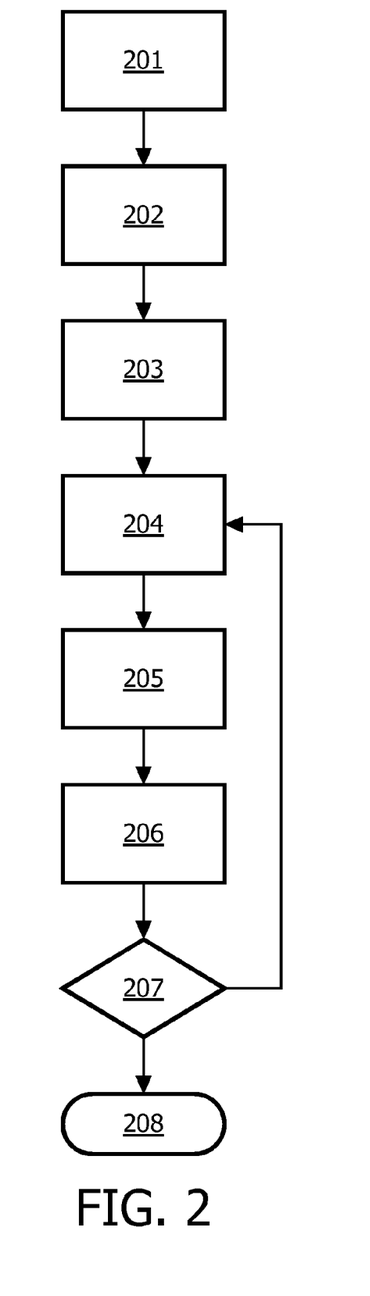
FIG. 2 is a flowchart of a method of displaying a set of interrelated objects.

FIG. 2 illustrates a method of displaying a set of interrelated objects. The method comprises step 201 of identifying a plurality of interrelated objects. In step 202, a first subset of the plurality of interrelated objects is selected for display based on a first information filter setting. In step 203, the first subset of the plurality of interrelated objects is displayed on a first display area. In step 204, a user is enabled to select a region of the first display area for enlargement by visually indicating the region in the first display area, wherein the user can select the region independently of locations of the displayed objects in the first display area. In step 205, a second subset of the plurality of interrelated objects is selected for display based on a second information filter setting, wherein the second information filter setting causes selection of objects corresponding to the selected region with an increased level of information detail compared to the first information filter setting. In step 206, the second subset of the plurality of interrelated objects is displayed on a second display area. In step 207, it is determined whether a new region is selected. If it is determined in step 207 that a new region is selected, the method returns to step 207. Otherwise, the method ends in step 208. The method may be implemented using a computer program product. Variations and additions to the method are within reach of the skilled person in view of the present description, including the description of the system.

An external computerized representation of the information related to a clinical guideline or pathway to be displayed and analyzed may be accessed to retrieve or identify the plurality of interrelated objects. The second displayer may provide a visual representation of the current focus of user attention that can be interactively navigated over an overview display of a clinical guideline or pathway, the overview display being provided by the first displayer. The second information filter selects the information to be displayed inside the visual representation of the current focus of user attention. A mechanism may be provided to select this information filter and adapt it to the current user role or target clinical context or task.

An external data base may be configured to store the information to be analyzed, e.g. the computerized guideline in form of a rule-based engine, the patient data via accessing an electronic medical record, institutional information via accessing an enterprise- or hospital-wide information system etc. From the computerized guideline representation, a flowchart-like overview of the major constituents of a clinical guideline or pathway may serve as the starting point of the first display area. Scope and level of detail comprised by this overview can be pre-instantiated according to user role or clinical task by an overview filter. The level of detail displayed may be adapted to the size of display space available and by what is needed for an overall orientation of the user in view of the target application.

The focus of attention may be selected by moving e.g. a "magnifying glass"-like object over the overview. In addition, more detailed information about the underlying portion of the guideline or pathway may be displayed inside the "magnifying glass". However, the display inside the "magnifying glass" is not just a magnified version of the original pixel pattern of the overview, but may contain additional pieces of information related to the underlying portion of the overview and selected in a both user- and task-specific way.

Different GUI manifestations of such a "magnifying glass" are envisaged. In its simplest form, a frame or window showing the detailed information is panning and zooming over the overview display in accordance with mouse-based interaction. In general, for example, any non-linear, sufficiently smooth mapping onto manifolds can be used. While panning the focus of user attention, the display is zooming in and out in conjunction with the detailed information fading in and out.

The additional information displayed inside the "magnifying glass" may be retrieved from the associated external data bases. A filter, e.g. in form of dedicated data base requests, may be used to retrieve the additional detailed information needed in view of the role of the user and the clinical target application. The information filter may be adapted to the role of the user and the clinical target application. This adaptation may take any one, or a combination of, the following forms:

selecting from a number of pre-defined filters according to the user authorization upon login. Different authorizations may be applied to different kinds of user, such as physician in charge of a patient, guest user, resident, fellow, hospital administrator, or quality manager.

selecting from a number of pre-defined filters according to the tasks being performed. Such a task may be defined by the state of a user interface, for example. Example tasks are analyzing individual patient paths in view of treatments applied, medication used, preparation of a tumor board, compiling statistical information about guideline adherence over patient groups, and monitoring of quality problems associated with specific decision points or treatment options selected.

allowing the user to select from pre-defined levels of detail, for example according to hierarchical decision levels in the guidelines, up-to-dateness of information, and/or quality of information.

allowing the user to select from pre-defined (clinical) categories, such as standardized quality/performance measures and therapeutic response criteria.

allowing the user to select from different domains, e.g. information relating to the personal performance, the performance of the department or hospital, information relating to patients managed by the individual, the department or the hospital.

automatically adapting the filter to the selections made by the users turning it into a "heuristically guided search engine" mining the available data along guidelines or pathways. This way, the system may automatically learn about important information and less important information by analyzing user interaction.

The definition of the pre-defined filters and information categories may be made during the installation of the system to address the details of the information and control flow of the particular institution.

Patient and quality management according to guidelines is important for modern healthcare management. The proposed smart guideline viewer can be used wherever guidelines and pathways are deployed, for example in oncology, neurology, cardiology, intensive care, chronic disease management etc. It can also be used in home care when integrated into the web browser used by a patient actively participating in his/her care management.

Figure 3:
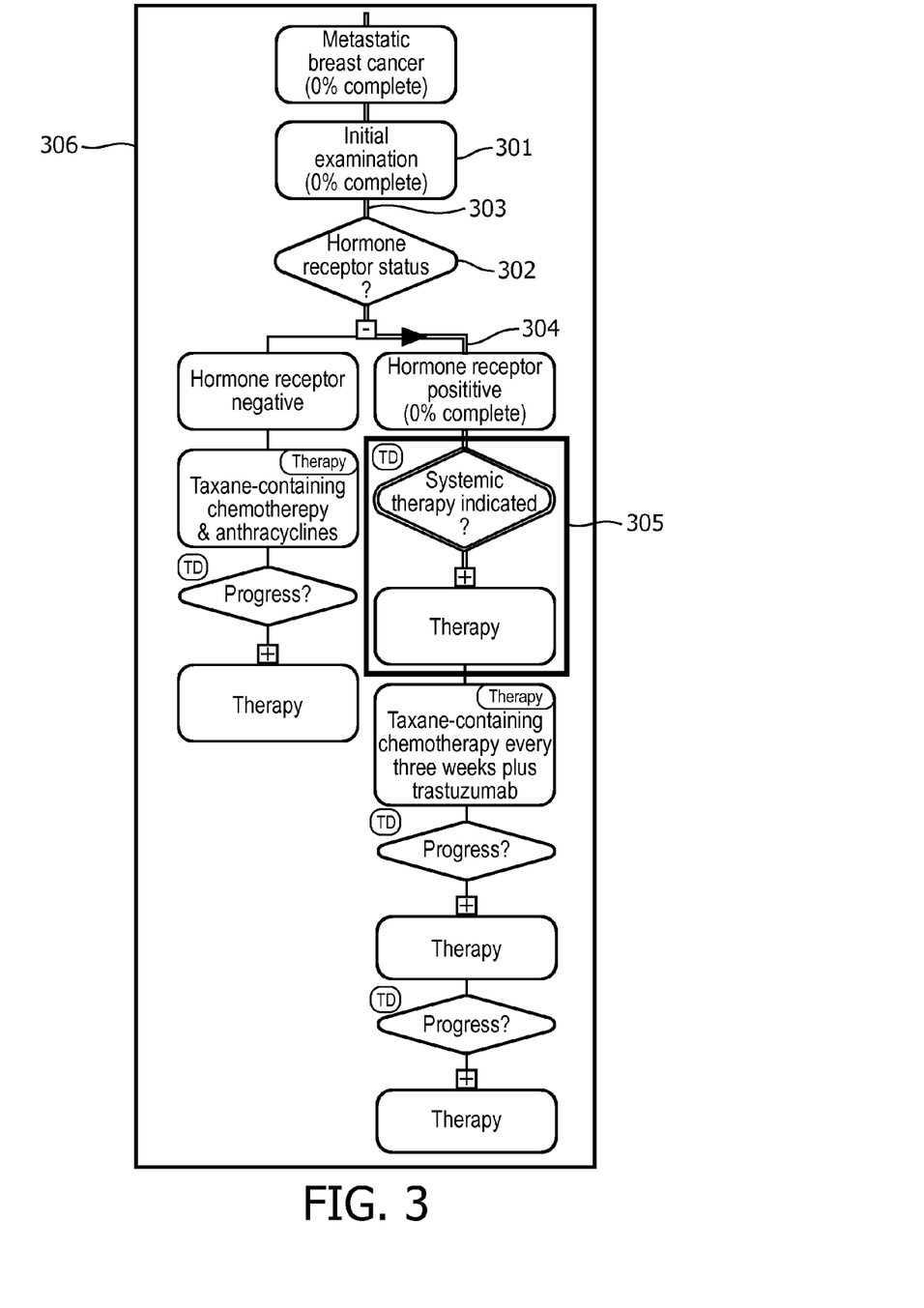
FIG. 3 is a sketch of a screen shot including a selected region.

FIG. 3 illustrates an example of what may be shown in a first display area 306. The figure shows a representation of a first subset of a plurality of interrelated objects. The interrelated objects are represented by graphical symbols, such as rectangles 301 and diamond shapes 302, and the relations are represented by interconnections such as lines 303 and arrows 304. As shown in FIG. 3, text may be provided inside the symbols 301, 302 to show further detail about the objects. The information has been filtered by the first information filter 2 before being displayed in the first display area. Consequently, not all of the objects in the plurality of interrelated objects are shown in FIG. 3. Some objects and/or relations may be omitted and/or some groups of objects may be collectively represented by a single object in the first subset shown in the first display area. FIG. 3 further shows a selected region 305. The extent of the selected region 305 is indicated by a rectangle. The region has been selected by means of user interface 7.

Figure 4:
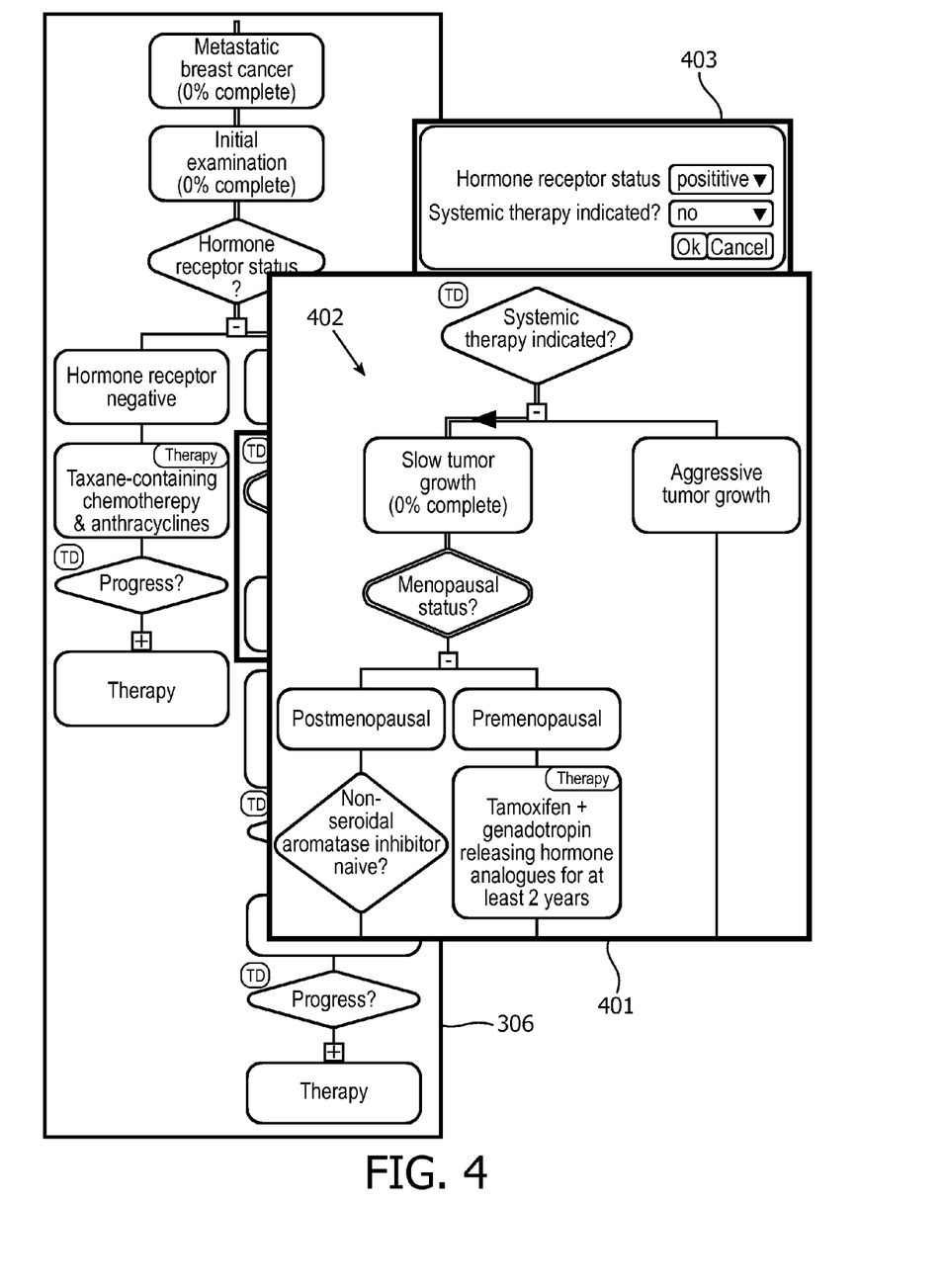
FIG. 4 is a sketch of a screen shot including an enlarged view of a selected region.

FIG. 4 illustrates an example of what may be shown in a second display area, in relation to the first display area 306, which is also shown in FIG. 3. The figure shows the first display area 306, as described in relation to FIG. 3. FIG. 4 further shows a second display area 401. The contents of the second display area 401 corresponds to the contents of the selected region 305. However, the second display area 401 shows more detail of the objects associated with the selected region 305. Consequently, the second display area 401 shows more representations of objects 402 than shown in the selected region 305 of the first display area 401. The objects 402 are selected by the second information filter 4. The selections made by the first information filter 2 and the second information filter 4 may be tailored to the task of the user of the system. In display area 403, the user may be enabled to input further information, for example by means of a drop down box, which may influence the display of objects in the second display area 401. This way, the display may be further personalized and/or adjusted to the particulars of the case at hand.

It will be appreciated that the invention also applies to computer programs, particularly computer programs on or in a carrier, adapted to put the invention into practice. The program may be in the form of a source code, an object code, a code intermediate source and object code such as in a partially compiled form, or in any other form suitable for use in the implementation of the method according to the invention. It will also be appreciated that such a program may have many different architectural designs. For example, a program code implementing the functionality of the method or system according to the invention may be sub-divided into one or more sub-routines. Many different ways of distributing the functionality among these sub-routines will be apparent to the skilled person. The sub-routines may be stored together in one executable file to form a self-contained program. Such an executable file may comprise computer-executable instructions, for example, processor instructions and/or interpreter instructions (e.g. Java interpreter instructions). Alternatively, one or more or all of the sub-routines may be stored in at least one external library file and linked with a main program either statically or dynamically, e.g. at run-time. The main program contains at least one call to at least one of the sub-routines. The sub-routines may also comprise calls to each other. An embodiment relating to a computer program product comprises computer-executable instructions corresponding to each processing step of at least one of the methods set forth herein. These instructions may be sub-divided into sub-routines and/or stored in one or more files that may be linked statically or dynamically. Another embodiment relating to a computer program product comprises computer-executable instructions corresponding to each means of at least one of the systems and/or products set forth herein. These instructions may be sub-divided into sub-routines and/or stored in one or more files that may be linked statically or dynamically.

The carrier of a computer program may be any entity or device capable of carrying the program. For example, the carrier may include a storage medium, such as a ROM, for example, a CD ROM or a semiconductor ROM, or a magnetic recording medium, for example, a flash drive or a hard disk. Furthermore, the carrier may be a transmissible carrier such as an electric or optical signal, which may be conveyed via electric or optical cable or by radio or other means. When the program is embodied in such a signal, the carrier may be constituted by such a cable or other device or means. Alternatively, the carrier may be an integrated circuit in which the program is embedded, the integrated circuit being adapted to perform, or to be used in the performance of, the relevant method.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A system for displaying a set of interrelated objects, comprising:
   one or more display devices;
   one or more computers configured to:
     identify a plurality of interrelated objects;
     select a first subset of the plurality of interrelated objects for display based on a first information filter setting;
     control the one or more display devices to display the first subset of the plurality of interrelated objects on a first display area;

select a second subset of the plurality of interrelated objects for display based on a second information filter setting;
control the one or more display devices to display the second subset of the plurality of interrelated objects on a second display area;
a user interface configured to enable a user to select any region including a plurality of objects of the first display area for enlargement by visually indicating the selected region in the first display area, wherein the user can select the region independently of individual locations of the displayed objects in the first display area, wherein the user interface is configured to enable the user to select a further region of the first display area for enlargement while the second subset of the plurality of interrelated objects is being displayed on the second display area;
wherein the second information filter setting is configured to select objects corresponding to the selected region with an increased level of information detail compared to the first information filter setting.

2. The system according to claim 1, wherein the second display area is centered around the selected region of the first display area.

3. The system according to claim 1, wherein the user interface is configured to enable the user to drag the selected region over the first display area.

4. The system according to claim 3, wherein the one or more computers are configured to update the display of the second display area in response to the user dragging the selected region over the first display area.

5. The system according to claim 1, wherein at least one of the plurality of interrelated objects is a composite object comprising a plurality of sub-objects, wherein the first information filter setting is configured to select the composite object, and wherein the second information filter setting is configured to select the composite object and at least one of the plurality of sub-objects comprised in the composite object.

6. The system according to claim 1, wherein
the plurality of interrelated objects are associated with respective object information detail levels;
the one or more computers are configured to:
identify a first information detail level threshold and a second information detail level threshold;
select the objects by comparing the respective object information detail levels with the first information detail level threshold; and
select the objects by comparing the respective object information detail levels with the second information detail level threshold.

7. The system according to claim 6, wherein the information represented by an interrelation between two objects is associated with a higher information detail level than the information represented by at least one of the two objects.

8. The system according to claim 1, wherein the one or more computers are configured to select a piece of textual information represented in the second subset of objects represented in the first subset of objects.

9. A system for displaying portions of a clinical guideline, comprising:
one or more display devices;
a database configured to store the clinical guidelines;
a user interface configured to receive inputs from a user;
one or more computer processors programmed to:
select and retrieve a first subset of objects of the clinical guideline from the database based on a first filter setting,
control the display device to display the first subset of objects in a first display area,
receive an input from the user interface indicating a region of the first display area which includes a plurality of the objects, the region being selected independently of individual locations of the displayed objects in the first display area,
select a second subset of objects of the clinical guideline using a second filter setting configured to select objects corresponding to the selected region of the clinical guideline with an increased level of information detail relative to the first filter setting,
control the one or more display devices to control the second subset in a second display area,
receive an input from the user interface indicating a further region of the first display area for enlargement while the second subset of objects of the clinical guideline are being displayed in the second display area,
receive an input from the user interface indicating that the selected region is to be dragged over the first display area, and
as the selected region is dragged over the first display area, accessing the database to retrieve additional clinical guideline information and applying the second filter setting to select objects corresponding to the dragged selected region with the increased level of detail compared to the first filter setting;
wherein the user interface is configured to enable the user to select a further region of the first display area for enlargement while the second subset of the plurality of interrelated objects is being displayed on the second display area.

10. The system according to claim 1, wherein the one or more computers are configured to control the display device to continue displaying the objects displayed on at least part of the first display area while displaying the second subset of the plurality of interrelated objects on the second display area.

11. A method of displaying a set of interrelated objects, comprising:
identifying a plurality of interrelated objects;
selecting a first subset of the plurality of interrelated objects for display based on a first information filter setting;
displaying the first subset of the plurality of interrelated objects in a first display area of one or more display devices;
enabling a user to select any region of the first display area for enlargement by visually indicating the selected region in the first display area using a user interface, wherein the selected region includes more than one object, wherein the user can select the selected region independently of individual locations of the displayed objects in the first display area;
selecting a second subset of the plurality of interrelated objects for display based on a second information filter setting, wherein the second information filter setting causes selection of objects corresponding to the selected region with an increased level of information detail compared to the first information filter setting; and
displaying the second subset of the plurality of interrelated objects on a second display area of the one or more display devices;
wherein the user interface is configured to enable the user to select a further region of the first display area for enlargement while the second subset of the plurality of interrelated objects is being displayed on the second display area.

12. A non-transitory computer-readable medium carrying instructions for causing a processor system to perform the method according to claim 11.

13. The method according to claim 11, further including:
receiving a selected second region of the first display area for enlargement from the user interface and continuing to display the second subset of interrelated objects in the second display area.

14. The method according to claim 11, further including:
receiving from the user interface, instructions to drag the selected region over the first display area.

15. The method according to claim 14, further including:
updating the display in the second display area in response to dragging the selected region over the first display area.

16. The method according to claim 11, wherein the plurality of interrelated objects are associated with respective object information detail levels, the method further including:
identifying a first information level threshold and a second information level threshold;
selecting the displayed objects by comparing the respective object information detail levels with the first information detail level threshold; and
selecting the objects to be displayed in the second display area by comparing the respective object information detail levels with the second information detail level threshold;
wherein the information represented by an interrelation between two objects is associated with a higher information detail level than the information represented by at least one of the two objects.

17. The method according to claim 11, wherein the set of interrelated objects includes one of a clinical guideline which define disease-specific clinical patient management step and a pathway which tracks patients through a plurality of management options offered by the guidelines, the clinical guideline or pathway being represented by boxes interconnected with lines.

\* \* \* \* \*